(12) United States Patent
Leo et al.

(10) Patent No.: US 10,631,926 B2
(45) Date of Patent: Apr. 28, 2020

(54) IRRIGATED FINNED ABLATION HEAD

(71) Applicant: St. Jude Medical Luxembourg Holding S.à.r.l., Luxembourg (LU)

(72) Inventors: Giovanni Leo, Cologny (CH); Nicolas Aeby, Geneva (CH)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 746 days.

(21) Appl. No.: 14/933,189

(22) Filed: Nov. 5, 2015

(65) Prior Publication Data

US 2016/0128768 A1 May 12, 2016

Related U.S. Application Data

(62) Division of application No. 13/104,726, filed on May 10, 2011, now Pat. No. 9,179,968.

(60) Provisional application No. 61/333,045, filed on May 10, 2010.

(51) Int. Cl.
   *A61B 18/14* (2006.01)
   *A61B 18/00* (2006.01)

(52) U.S. Cl.
   CPC . *A61B 18/1492* (2013.01); *A61B 2018/00011* (2013.01); *A61B 2018/00029* (2013.01); *A61B 2218/002* (2013.01)

(58) Field of Classification Search
   CPC .......... A61B 18/1492; A61B 2218/002; A61B 2018/00011; A61B 2018/0002
   See application file for complete search history.

(56) References Cited

U.S. PATENT DOCUMENTS

| | | | |
|---|---|---|---|
| 4,532,924 A | 8/1985 | Auth et al. | |
| 4,606,331 A | 8/1986 | Shene | |
| 4,844,099 A | 7/1989 | Skalsky et al. | |
| 5,240,070 A | 8/1993 | Ryan | |
| 5,423,811 A | 6/1995 | Imran et al. | |
| 5,441,498 A | 8/1995 | Perkins | |
| 5,454,782 A | 10/1995 | Perkins | |

(Continued)

FOREIGN PATENT DOCUMENTS

| | | |
|---|---|---|
| EP | 2382935 A1 | 11/2011 |
| WO | 2008147599 A1 | 12/2008 |
| WO | 2009023385 A1 | 2/2009 |

*Primary Examiner* — Michael F Peffley
*Assistant Examiner* — Yasamin Ekrami
(74) *Attorney, Agent, or Firm* — Dykema Gossett PLLC

(57) ABSTRACT

An irrigated finned ablation head that provides enhanced cooling. The irrigated finned ablation head comprises a plurality of radial fins that are distributed about a central axis and that extend axially from a common base. The plurality of fins are arranged to define a central passageway along the central axis, as well as a plurality of slots therebetween, the slots extending in an axial direction along the irrigated finned ablation head. In one embodiment, the central passageway extends through the irrigated finned ablation head, defining an opening at the distal extremity, with the slots extending from the base to the opening. In another embodiment, the irrigated finned ablation head includes a cap portion at a distal portion that is common to all the radial fins, so that the slots are terminated at the distal portion of the irrigated finned ablation head. The radial flow distribution along the central axis can be tailored by the configuration of the central passageway.

11 Claims, 6 Drawing Sheets

(56) References Cited

U.S. PATENT DOCUMENTS

| | | |
|---|---|---|
| 5,643,197 A | 7/1997 | Brucker et al. |
| 5,658,278 A | 8/1997 | Imran et al. |
| 5,735,342 A | 4/1998 | Nitta |
| 5,779,699 A | 7/1998 | Lipson |
| 5,913,854 A | 6/1999 | Maguire et al. |
| 6,017,338 A | 1/2000 | Brucker et al. |
| 6,019,756 A | 2/2000 | Mueller et al. |
| 6,032,674 A | 3/2000 | Eggers et al. |
| 6,120,476 A | 9/2000 | Fung et al. |
| 6,168,415 B1 | 1/2001 | Pleasant et al. |
| 6,171,275 B1 | 1/2001 | Webster, Jr. |
| 6,217,573 B1 | 4/2001 | Webster |
| 6,231,595 B1 | 5/2001 | Dobak, III |
| 6,241,724 B1 * | 6/2001 | Fleischman ........ A61B 18/1492 600/374 |
| 6,258,087 B1 | 7/2001 | Edwards et al. |
| 6,522,930 B1 | 2/2003 | Schaer et al. |
| 6,569,162 B2 | 5/2003 | He |
| 6,602,242 B1 | 8/2003 | Fung et al. |
| 6,611,699 B2 | 8/2003 | Messing |
| 6,905,495 B1 | 6/2005 | Fuimaono et al. |
| 7,004,923 B2 | 2/2006 | Deniega et al. |
| 7,104,989 B2 | 9/2006 | LaCroix |
| 7,163,537 B2 | 1/2007 | Lee et al. |
| 7,166,105 B2 | 1/2007 | Mulier et al. |
| 7,311,708 B2 | 12/2007 | McClurken |
| 7,364,578 B2 | 4/2008 | Francischelli et al. |
| 7,406,999 B2 | 8/2008 | Bhatti et al. |
| 7,422,588 B2 | 9/2008 | Mulier et al. |
| 7,435,250 B2 | 10/2008 | Francischelli et al. |
| 7,537,595 B2 | 5/2009 | McClurken |
| 7,615,049 B2 | 11/2009 | West et al. |
| 7,625,372 B2 | 12/2009 | Esch et al. |
| 8,755,861 B2 | 6/2014 | Harlev et al. |
| 2002/0120262 A1 | 8/2002 | Bek et al. |
| 2003/0130650 A1 | 7/2003 | Yaron |
| 2003/0176791 A1 | 9/2003 | Rabiner et al. |
| 2003/0181897 A1 | 9/2003 | Thomas |
| 2003/0225403 A1 | 12/2003 | Woloszko et al. |
| 2004/0116920 A1 | 6/2004 | Rioux et al. |
| 2004/0220557 A1 | 11/2004 | Eum |
| 2005/0177148 A1 | 8/2005 | Van Der Walt |
| 2005/0203505 A1 | 9/2005 | Megerman et al. |
| 2005/0222564 A1 | 10/2005 | Plaza |
| 2005/0234446 A1 | 10/2005 | Van Wyk |
| 2006/0149192 A1 | 7/2006 | Deniega |
| 2007/0185380 A1 | 8/2007 | Kucklick |
| 2008/0033423 A1 | 2/2008 | Peacock, III |
| 2008/0091193 A1 | 4/2008 | Kauphusman |
| 2008/0125809 A1 | 5/2008 | Suzuki et al. |
| 2008/0161792 A1 | 7/2008 | Wang |
| 2008/0161794 A1 | 7/2008 | Wang |
| 2008/0161800 A1 | 7/2008 | Wang |
| 2008/0249522 A1 | 10/2008 | Pappone |
| 2008/0294144 A1 | 11/2008 | Leo |
| 2008/0294158 A1 | 11/2008 | Pappone |
| 2008/0319376 A1 | 12/2008 | Wilcox et al. |
| 2009/0093811 A1 | 4/2009 | Koblish |
| 2009/0143760 A1 | 6/2009 | Van Dam |
| 2009/0143779 A1 | 6/2009 | Wang |
| 2009/0163912 A1 * | 6/2009 | Wang ................ A61B 18/1492 606/41 |
| 2009/0163913 A1 | 6/2009 | Wang |
| 2009/0287092 A1 | 11/2009 | Leo |
| 2010/0030209 A1 | 2/2010 | Govari |
| 2010/0057072 A1 | 3/2010 | Roman et al. |
| 2010/0057073 A1 | 3/2010 | Roman et al. |
| 2010/0057074 A1 | 3/2010 | Roman |

\* cited by examiner

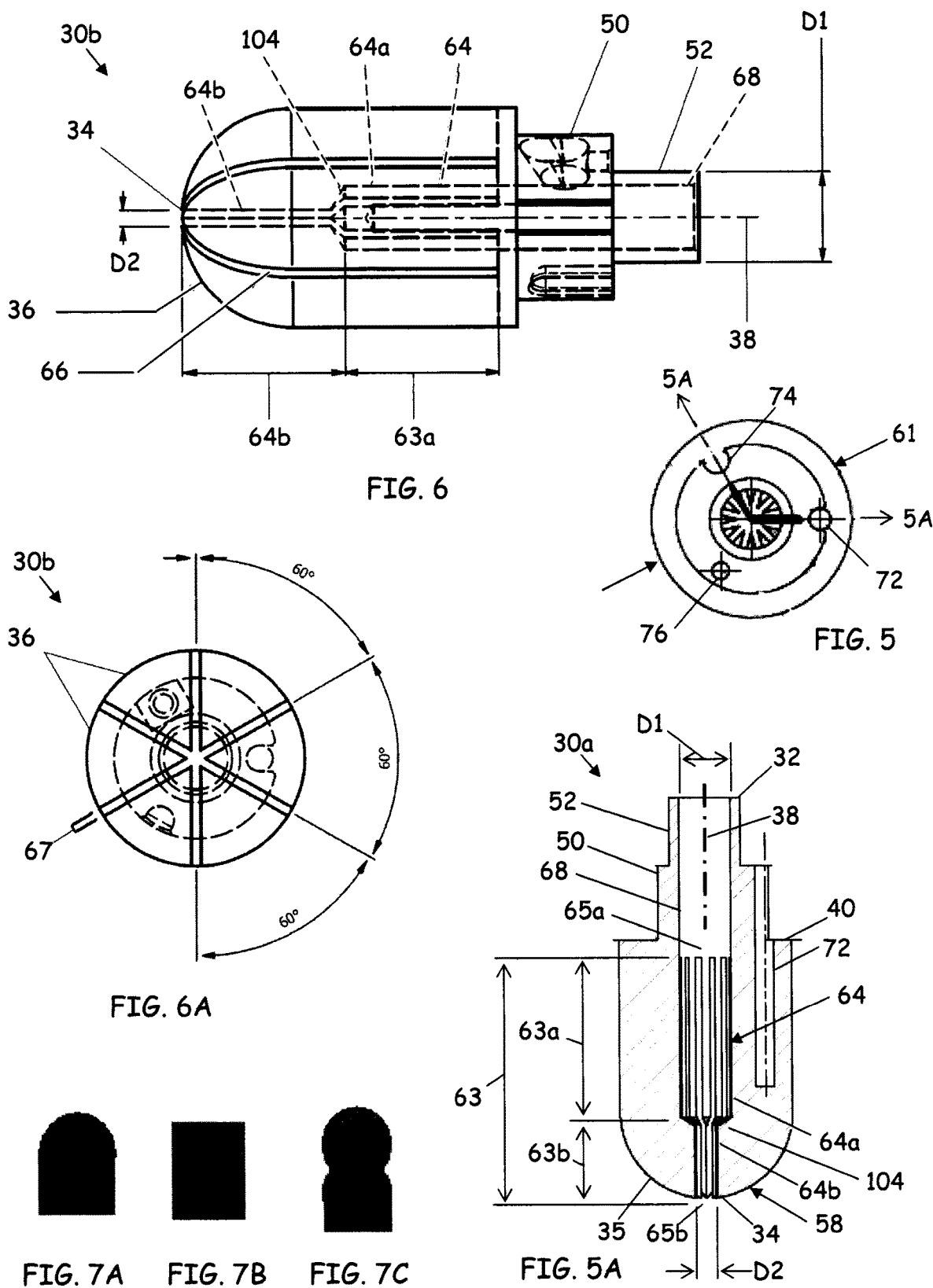

IRRIGATED FINNED ABLATION HEAD

RELATED APPLICATIONS

This application is a divisional of U.S. patent application Ser. No. 13/104,726, filed 10 May 2011 (the '726 application), now U.S. Pat. No. 9,179,968, issued 10 Nov. 2015, which claims priority from provisional application No. 61/333,045, filed 10 May 2010 (the '045 application). The '726 application and the '045 application are hereby incorporated by reference as though fully set forth herein.

FIELD OF THE DISCLOSURE

The present invention relates to methods and devices for performing minimally invasive ablative procedures within mammalian bodies. Specifically, the present invention relates to methods and devices that implement an irrigated finned ablation head for enhanced cooling features for temperature control of irrigated ablation heads and prevention of blood coagulation and other complications resulting ablative procedures.

BACKGROUND OF THE DISCLOSURE

An ablation catheter is a catheter having an end effector, such as a radio-frequency (RF) ablation head, designed to deliver energy to a target tissue for the purpose of forming a lesion on the target tissue. Catheter-based ablation therapy is performed by accessing the target tissue via a biological lumen, such as a blood vessel. The ablation head is often cooled with irrigation fluids to control the temperature of the ablation head. In some systems, the irrigation fluid is vented into the biological lumen or targeted organ via apertures in the ablation head. The local venting of irrigation fluid through the ablation head can serve the function of purging the immediate area of the target tissue, thereby preventing recirculation of blood proximate the ablation head that can lead to coagulation and the formation of blood clots.

An existing paradigm in irrigated ablation head design is to provide uniform flows through the purged apertures. For example, U.S. Patent Application Publication No. 2010/0030209 to Govari et al. (Govari) discloses an ablation catheter having a distal tip with a plurality of perforations through the outer surface, which are distributed circumferentially and longitudinally over the distal tip. Govari discloses that the perforations may optionally be varied over the length of the distal tip to compensate for pressure variation and ensure equal flow over the entire length. For this purpose, the perforations at and near the most distal part of the tip may be made larger than the more proximal perforations, which are nearer to the fluid inlet. As further example of the emphasis on uniform flow, U.S. Pat. No. 6,017,338 to Brucker, et al. discloses structures to uniformly and evenly distribute the fluid around tip structures.

U.S. Patent Application Publication No. 2008/0249522 to Pappone et al. discloses internal lumen designs in an irrigated catheter that promotes uniform cooling and/or uniform fluid distribution in longitudinally spaced apart elution holes by varying the diameter of a fluid delivery lumen.

Other designs, such as U.S. Pat. No. 7,104,989 to Skarda (Skarda) deliver greater flow to the tip region of the irrigated ablation head. Skarda discloses a plurality of pores arrayed longitudinally and circumferentially around all sides of the ablation head, with an increased density of pores in distal end region of the ablation head, thus concentrating delivery of a conductive fluid distally, where primary contact with the target tissue occurs.

Despite such designs, problems persist in the implementation of irrigated ablation heads. Such problems include coagulation of blood in recirculation zones about the ablation head that can lead to the formation of blood clots. There is need for an irrigated ablation catheter and system that mitigates these shortcomings.

SUMMARY OF THE DISCLOSURE

In various embodiments of the invention, a finned ablation head that generates non-uniform velocity/flow profile is disclosed wherein the flow and the attendant convective cooling is actually greater near the proximal portion of the irrigated ablation head than at the distal extremity. While cooling flow is still provided to the distal extremity of the finned ablation head, various embodiments of the design of the fins also take advantage of the conduction of heat away from the distal extremity to the higher convective cooling regions at the proximal end of the irrigated finned ablation head.

Another aspect of the finned ablation head provides that the slots between the fins can be dimensioned to provide the same or higher effusion velocities from the ablation head at irrigation flow rates that are lower than existing ablation heads. An additional characteristic of this aspect is that higher pressures of operation can be realized, thus providing more reliable purging of the effusion passages. The enhanced efficiency of the cooling of the irrigated finned ablation head enables a reduced flow rate can be maintained at the same power levels as existing irrigated ablation heads to provide more operating time in the patient before reaching the limit of irrigation fluid that is introduced into the patient (presently established at about 1 liter). Alternatively, operation at higher power levels can be performed while requiring only the same irrigation flow rate as existing ablation heads. The irrigated finned ablation head can also be tailored for a radial flow having other desired flow distributions (e.g., substantially uniform velocity profiles) about the exterior tissue-contacting surfaces.

Structurally, various embodiments of the irrigated finned ablation head include a plurality of axially extending radial fins that are uniformly distributed about a central axis and that extend from a common base. The plurality of fins are arranged to define a central passageway along the central axis, as well as a plurality of axially-elongated slots therebetween that extend along the irrigated finned ablation head. In one embodiment, the central passageway extends through the irrigated finned ablation head, defining an opening at a distal extremity, with the slots extending from the base to the opening. In another embodiment, the irrigated finned ablation head includes a cap portion at a distal portion that is common to all the radial fins, so that the slots are terminated at the distal portion of the irrigated finned ablation head.

In various embodiments of the invention, irrigation fluid is introduced into the central passageway of the irrigated finned ablation head, exiting via the axially-elongated slots and, when present, the opening at the distal extremity. The radial flow distribution along the central axis can be tailored by the configuration of the central passageway. In some embodiments, the central passageway comprises a proximal portion proximate to the base of the ablation head having a first diameter and a distal portion proximate to the tip of the ablation head having an effective second diameter that is smaller than the first diameter. The length of the first portion relative to the second portion can be tailored to provide the desired flow characteristics through the axially-elongated slots.

For example, in certain embodiments of the irrigated finned ablation head implementing radial fins that extend all the way to the distal extremity of the ablation head, it has been found by computer simulation that where the proximal portion and the distal portion are approximately equal (i.e., a length ratio of approximately 1:1), the flow distribution along the length of the axially-elongated slots is substantially uniform. For certain applications, such uniform flow characteristics may be desired.

In other embodiments, implementation of a shorter length for the proximal portion, in conjunction with a longer distal portion of smaller effective diameter, can cause an increase in the exiting radial flow of the irrigation fluid proximate to the base of the ablation head. Accordingly, there is a higher velocity flow, as well as a greater flow rate, through the proximate portion than through the distal portion of the ablation head. The convection coefficient is therefore greater near the base of the fin than at the distal portion of the fin. These effects can be further enhanced by the selection of slot geometries (number of slots and their width).

Such a flow distribution is counter to existing paradigms of promoting a uniform flow distribution or increasing the flow at the distal extremity of an irrigation head to the detriment of the cooling of the proximal portion of the ablation head. Nevertheless, it is believed that this approach can adequately cool the ablation head/target tissue interface while at the same time providing both better cooling of the proximal portion of the ablation head and greater purging of the areas near the proximal portion of the ablation head to prevent blood coagulation. First, the base of the irrigated finned ablation head will run cooler during ablative operations, so that heat is conducted axially away from the distal portion of the ablation head to the cooler proximal portion. As such, blood that contacts base portion is not subjected to as high a temperature, thereby abating coagulation. Furthermore, with ablation heads that extend all the way to the distal extremity of the irrigated finned ablation head, there is active convective cooling of the distal portions of the fins. Second, the non-uniform velocity profile promotes more active purging of the area surrounding the proximal portion of the head, which is where stagnation can lead to blood coagulation. Hence, the non-uniform velocity profile disclosed herein provides for adequate and reliable cooling of the distal extremity of the ablation head/target tissue interface, while providing lower temperatures and higher purging flows at the base of the ablation head to prevent recirculation and attendant blood coagulation.

Structurally, specific embodiments of the invention include a base portion defining an outer diameter centered about a central axis, the central axis being substantially normal to the base portion, with the base portion defining an opening that extends through the base portion into the irrigated finned ablation head. A plurality of radial fins extend parallel to the central axis from the base portion, the fins being distributed about the central axis to define a plurality of slots therebetween. The plurality of radial fins and the opening of the base portion are configured and arranged to define a central passageway that extends at least partway into the irrigated finned ablation head. The central passageway is in fluid communication with the plurality of slots and can include a proximal portion that defines a first diameter. In one embodiment, the irrigated finned ablation head defines a cylindro-spherical profile having an overall length dimension along the central axis, the cylindro-spherical profile being adapted to contact a target tissue. The base and the plurality of radial can define an exterior surface of the cylindro-spherical profile. The irrigated finned ablation head can be fabricated from materials commonly used for ablation, such as gold, a platinum-iridium alloy, or a stainless steel alloy.

The irrigated finned ablation head can be configured so that the central passageway includes a distal portion that defines a second diameter, the second diameter being less than the first diameter. In one embodiment, the distal portion of the central passageway defines an opening at the distal extremity of the irrigated finned ablation head. In one embodiment, the proximal portion of the central passageway extends less than ½ of the overall length dimension of the irrigated finned ablation head. In other embodiments, the proximal portion of the central passageway extends over more than 5% of the overall length dimension. In some configurations, the number of radial fins can be three or greater, in other embodiments, the number of radial fins can be twelve or less. Each of the plurality of radial fins can include radiused breaks that transition between the exterior surface of the cylindro-sperical profile and the plurality of slots defined between the plurality of radial fins.

In some embodiments, the plurality of radial fins extend to a distal extremity of the irrigated finned ablation head. Optionally, the radial fins can be uniformly distributed about the central axis, and the slots defined therebetween of substantially equal dimension. In other embodiments, a cap portion is included at a distal portion of the irrigated finned ablation head. The cap portion can be unitary with the plurality of radial fins, or joined as a separate piece by brazing, soldering or other fusion process.

In another embodiment of the invention, the irrigated finned ablation head is utilized in a catheter-based RF ablation system that includes a flexible elongate body having a proximal end and a distal end, with the irrigated finned ablation head operatively coupled with the distal end of the flexible elongate body. A power supply line can be operatively coupled with the irrigated finned ablation head, the power supply line extending through the flexible elongate body and exiting the proximal end of the flexible elongate body for operative coupling with a power source. The catheter-based RF ablation system can also include a fluid supply line in fluid communication with the central passageway of the irrigated finned ablation head, the fluid supply line extending through the flexible elongate body and exiting the proximal end of the flexible elongate body for operative coupling with an irrigation source. In another embodiment of the invention, the catheter-based RF ablation system is provided with a set of instructions on a tangible medium, the instructions including connecting the power supply line to a power source connecting the fluid supply line to an irrigation source. The instructions can further include initiating a flow of fluid from the irrigation source that flows through the fluid supply line and through the irrigated finned ablation head, energizing the irrigated finned ablation head with the power source through the power supply line.

In another embodiment of the invention, a method of cooling an ablation head is practiced. The method includes forming a passageway that extends through a base portion of the ablation head and at least partially into the ablation head, the passageway extending along a central axis of the ablation head. A plurality slots are also formed on the ablation head, each of the plurality of slots having a slot length and passing laterally through the ablation head and defining a plane that is inclusive of a central axis of the ablation head, the plurality of slots being in fluid communication with the passageway and defining a plurality of radial fins that are distributed about the central axis, the slots and the passageway being dimensioned to provide a flux profile that has a greater flow rate over the ⅓ of the slot length that is proximal to the base portion than over the ⅔ of the slot length that is distal to the base portion.

The above summary of the various representative embodiments of the invention are not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

FIG. 5 is a top view of the irrigated finned ablation head of FIG. 1;

FIG. 5A is a sectional view of the irrigated finned ablation head of FIG. 5;

FIG. 6 is a side view of a irrigated finned ablation head having six radial fins in an embodiment of the invention;

FIG. 6A is an end view of the irrigated finned ablation head of FIG. 6;

FIGS. 7A, 7B and 7C are profile views of various irrigated finned ablation head s in embodiments of the invention;

DETAILED DESCRIPTION

Figure 1:
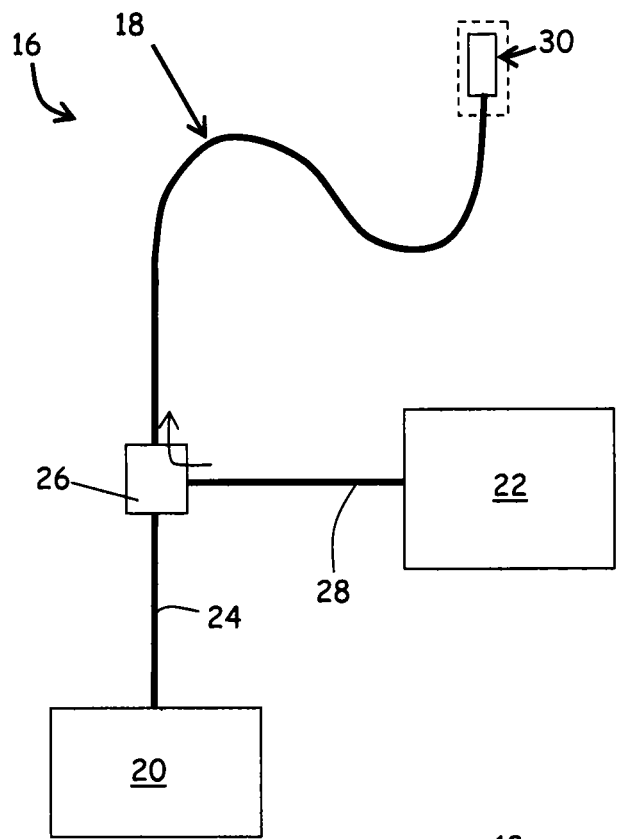
FIG. 1 is a schematic view of an ablation catheter system according to an embodiment of the invention.
Figure 1A:
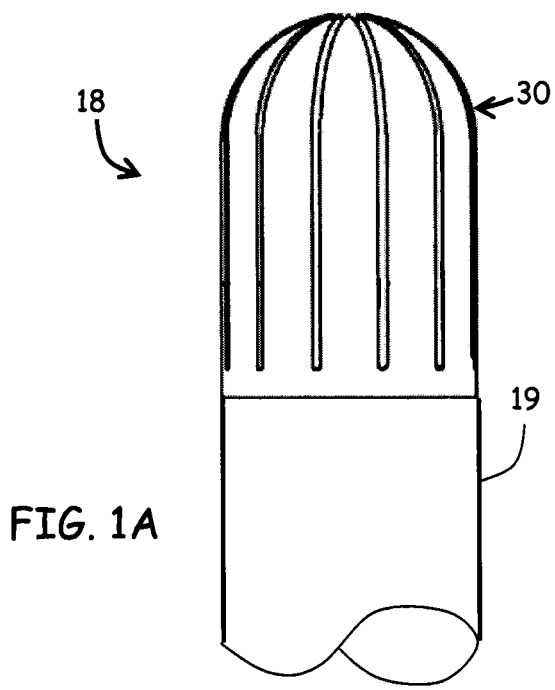
FIG. 1A is an enlarged side view of the irrigated finned ablation head depicted in FIG. 1.
Figure 2A:
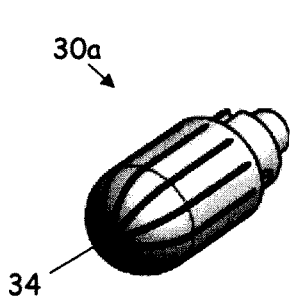
FIG. 2A is a perspective view of the irrigated finned ablation head in an embodiment of the invention.
Figure 2B:
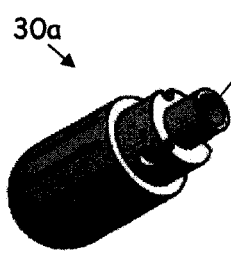
FIG. 2B is a second perspective view of the irrigated finned ablation head of FIG. 2A.
Figure 3A:
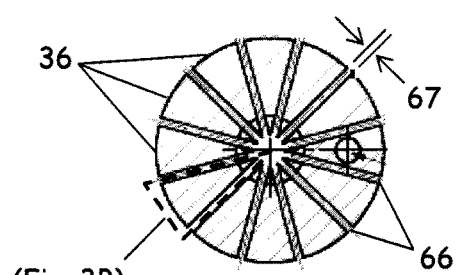
FIG. 3A is a sectional view of the irrigated finned ablation head of FIG. 3.
Figure 3:
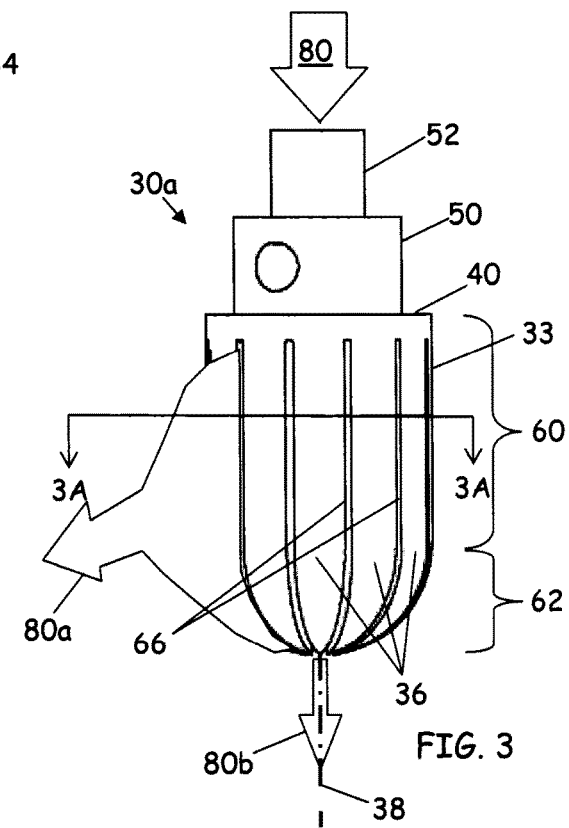
FIG. 3 is an elevation view of the irrigated finned ablation head of FIG. 1.
Figure 3B:
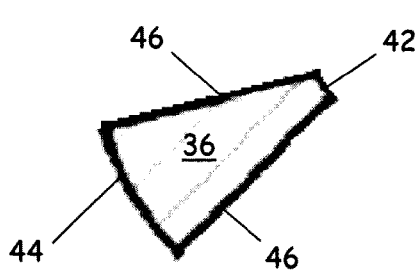
FIG. 3B is a sectional view of a radial fin of FIG. 3A.

Referring to FIG. 1, an ablation catheter system 16 having a catheter 18 having an elongated, flexible shaft 19 and an irrigated finned ablation head 30 positioned at one end of the flexible shaft 19. Herein, several embodiments of the irrigated finned ablation head 30 are presented, designated specifically by letter suffix (e.g., "30a") and referred to collectively by numerical reference 30. The catheter system 16 can further comprise a power supply 20 for powering the irrigated finned ablation head 30 and an irrigation supply 22 for providing fluids to the irrigated finned ablation head 30. In an embodiment of the invention, the catheter system 16 can further comprise a thermocouple lead extending from proximate to the irrigated finned ablation head 30 through the other end of the flexible shaft 19. The elongated catheter 18 defines an internal lumen for receiving a power supply line 24 linking the irrigated finned ablation head 30 to the power supply 20. Similarly, the internal lumen can also channel irrigation fluids from the irrigation supply 22 to the irrigated finned ablation head 30. In one embodiment, the catheter system 16 can further comprise a junction assembly 26 for feeding the power supply line 24 into the internal lumen and for joining a fluid supply line 28 from the irrigation supply 22 to the internal lumen.

Referring to FIGS. 2-5, an irrigated finned ablation head 30a having a proximal end 32 at a proximal portion 33 and a distal end or distal extremity 34 at a distal portion 35 is depicted in an embodiment of the invention. The irrigated finned ablation head 30a comprises a plurality of axially extending radial fins 36 that extend radially outward from a central axis 38. In this embodiment, the radial fins 36 extend axially from a base portion 40 to the distal extremity 34. Each of the radial fins 36 has an interior face 42, and exterior face 44, and radial or slot faces 46. In one embodiment, the irrigated finned ablation head 30a includes a first collar 50 and a second collar 52 that extend proximally from the base portion 40. The first and second collars 50 and 52 provide structure for attachment of various appurtenances. For example, the first collar may be used for attachment of a catheter shaft (not depicted), and the second collar may be used for attachment of an irrigation tube (not depicted).

In the depicted embodiment, the plurality of radial fins 36 define a cylindro-spherical profile 58 comprising a cylindrical portion 60 having an outer cylindrical diameter 61 and a substantially spherical portion 62, the spherical portion 62 being at the distal portion 35 of the irrigated finned ablation head 30. The interior faces 42 of the radial fins 36 define a central passageway 64 that extends axially along the length of the radial fins 36, defining an opening 65a through the base portion 40 and an opening 65b at the distal extremity 34 of the irrigated finned ablation head 30a. In one embodiment, the central passageway 64 includes a proximal portion 64a having a length 63a and diameter D1, and a distal portion 64b having a length 63b and diameter D2 that is different from the diameter D1, the lengths 63a and 63b making up the total length of the central passageway 64 between openings 65a and 65b. In some embodiments, the distal portion 64a of the central passageway 64 is not individually formed, but rather is the result of the confluence of the plurality of slots 66, particularly when the radial fins 36 extend to the distal extremity 34, as with the irrigated finned ablation head 30a. In such embodiments, the diameter D2 will be a function of the slot widths 67.

The confluence of the plurality of slots 66 also provides enhanced convective cooling at the distal tip 34 of the irrigated finned ablation head 30a, where current density tends to be highest during the ablation procedure. Enhanced cooling of the zone where current densities are highest helps control the temperature at a contact interface 70 between the irrigated finned ablation head 30a and a target tissue 31, and to eliminate hot spots.

The radial slot faces 46 of adjacent fins 36 define a plurality of slots 66, each of the slots 66 being defined between adjacent fins 36 and having a tangential dimension or slot width 67. Optionally, the plurality of radial fins 36 can be arranged so that the slot widths 67 are substantially equal. A central lumen 68 extends through the first and second collars 50 and 52 along the central axis 38 and is in fluid communication with the central passageway 64.

The irrigated finned ablation head 30a can also include ports 72, 74 and 76 that extend substantially parallel to the central axis 38. In the depicted embodiment, port 72 is a thermowell for accommodation of a temperature sensor (not depicted), port 74 is a solder or weld port for attachment of a power lead (not depicted) and port 76 is for attachment of a retrieval string (not depicted).

The irrigated finned ablation head 30a can be fabricated from materials known to the artisan, such as platinum-iridium, gold and stainless steel. The radial fins 36 can be formed from a solid cylindro-spherical plug by forming the central passageway 64 and central lumen 68 therein and forming the plurality of slots 66 across the outer cylindrical diameter 61 of the cylindro-spherical plug. The radial fins 36 can be finished to remove sharp edges by processes such as deburring ultrasonically with a powder or by electropolishing. The exterior surfaces 44 are tailored for contact with a target tissue.

In one embodiment, bulk mechano-chemical polishing is applied to the irrigated finned ablation head 30a to reduce or contour the angles and edges that define the slots 66 in a process called "trovalisation." The trovalisation conditions the edges of the radial fins 36 with breaks of approximately 1-3 μm to prevent hot spots that can arise at sharp corners that bear an electrical current. The breaks also can help prevent lacerations to the target tissue as well as to the biological lumen(s) through which the irrigated finned ablation head 30a traverses.

In operation, the exterior surfaces 44 of the radial fins 36 are brought into contact with the target tissue. A flow of irrigation fluid 80 is introduced into the central lumen 68 and enters the central passageway 64 of the irrigated finned ablation head 30a. A first portion 80a of the flow of irrigation fluid 80 entering the central passageway 64 flows radially outward through the plurality of slots 66 between the radial slot faces 46 of the adjacent radial fins 36. A second portion 80b of the flow of irrigation fluid 80 entering the central passageway exits the irrigated finned ablation head 30a via the opening 65b at the distal extremity 34.

Figure 4:
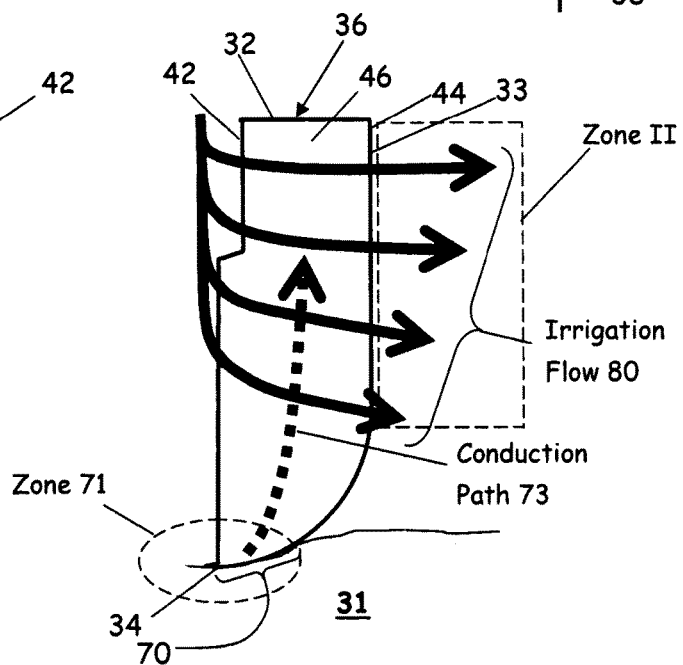
FIG. 4 depicts the fin effect of a radial fin in an embodiment of the invention.

The "fin effect" caused by each of the plurality of radial fins 36 is depicted in FIG. 4. The radial fin 36 is brought into contact with the target tissue 31, typically with the distal extremity 34 of the radial fin 36 contacting the target tissue 31. Electrical current flows through the radial fin 36 and passes through the contact interface 70 into the target tissue 31. There can be an increase locally in the electrical resistance at the contact interface 70 that causes an increase in the joule heating at the contact interface 70, which can result in a zone 71 of high joule heating.

The fin effect augments the cooling of zone 71. The interior faces 42 and the radial slot faces 46 of the radial fins 36 provide heat transfer surfaces that are bathed or swept with the flow of irrigation fluid 80 passing through the slots 66, providing enhanced cooling of the proximal portion 33 of the radial fin 36. The enhanced cooling of the proximal portion 33 causes heat to be transferred away from zone 71 via a conduction path 73. In this way, each of the plurality of radial fins 36 acts as a classical extended surface to the interface 70 that transfers energy by conduction within its boundaries, as well as transferring heat by convection across between its boundaries and the surroundings.

The radial fins 36 can be sized for a desired surface area-to-volume ratio A/V. The larger the A/V, the cooler the operating temperature of the fin. However, a tradeoff is that smaller fin volumes can also represent a narrower conduction path between zone 71 and the proximal portion 33 of the radial fin 36. These factors, along with the conductivity of the materials, warrant consideration in configuration of the radial fins 36.

Furthermore, the sizing and arrangement of the radial fins 36 can be configured to provide certain flow and heat transfer characteristics as the flow of irrigation fluid 80 flows over the radial fins 36. The spacing between adjacent radial fins 36 (i.e. the tangential dimensions of the slots 66) can be sized to provide desired resistance to flow and certain heat transfer characteristics. The smaller the slot width 67 between adjacent radial fins 36, the greater the resistance to flow. Also, for a given flow rate, the smaller the slot width 67 the greater the flow velocity of the flow of irrigation fluid 80 therethrough. Higher flow velocities tend to produce higher convection coefficients between the flow of irrigation fluid 80 and the heat transfer surfaces (i.e., the interior faces 42 and the radial slot faces 46).

Accordingly, the slot widths 67 can be tailored to produce a flow resistance that enables adequate flow of irrigation fluid 80 using standard irrigation pumps available to the artisan (typically having 3 to 4 bars operating pressure) while enhancing the heat transfer coefficient over a large surface area-to-volume ratio A/V. Proper sizing of the A/V of the radial fins 36 and the slot width 67 of the slots can control the temperature and the temperature profile of the irrigated finned ablation head 30a.

The surface area-to-volume ratio A/V can also be varied by the number of radial fins 36 within a given outer cylindrical diameter 61. That is, the greater the number of radial fins 36, the greater the surface area-to-volume ratio A/V. However, other considerations place practical limitations on the number of radial fins that can be placed within a given cylindro-spherical envelope. These considerations include the structural integrity so that the radial fins 36 do not fracture or break off during an ablation procedure, as well as the external area 44 required after formation of the slots 66 for effective delivery of the ablation energy.

An example and non-limiting configuration for the irrigated finned ablation head 30a was constructed and tested. The test results are included in U.S. Provisional Application No. 61/333,045, incorporated by reference above. The configuration included twelve radial fins 36 uniformly distributed about the central axis 38 and defined the outer cylindrical diameter 61 at approximately 2.3 mm for the cylindrical portion 60 of the irrigated finned ablation head 30a and a diameter of approximately 0.7 mm for the central lumen 68 and central passageway 64. The tangential dimension of the slots 66 for the example configuration were nominally 0.08 mm.

Referring to FIGS. 6 and 6A, a finned ablation head 30b that utilizes six radial fins 36 uniformly distributed about the central axis 38 is depicted in an embodiment of the invention. Generally, the deformation of the fins 36 can cause the slot widths 67 to change, thus altering the velocity profile of the fluid exiting the irrigated finned ablation head 30b. Functionally, for a given outer cylindrical diameter 61, a reduced number of fins 36 provides for fins that are thicker (i.e., radial fins with greater arc lengths along the interior face 42 and external area 44). Increasing the thickness reduces deformation of the fins 36, which better maintains the slot widths 67 when the irrigated finned ablation head 30b is placed under a contact force. While the use of fewer, larger fins 36 is provides radial fins 36 that are more rigid, there are also fewer slots 66 to cool larger fins, which can reduce the convective cooling of the radial fins 36. However, thicker fins also conduct heat in an axial direction more effectively. Therefore, by cooling the proximal portion 33 of the irrigated finned ablation head with an enhance convective coupling, better heat conduction away from the distal portion 35 of the irrigated finned ablation head 30b can be effected. These factors can be balanced against the type of materials used (thermal conductivity and material strength), the amount of cooling required and operational considerations.

Referring to FIGS. 7A through 7C, example profiles of the irrigated finned ablation head are represented. The cylindrospherical profile, which is utilized in the discussions of this application, is depicted in FIG. 7A. Other profiles can also be implemented for this invention, including, but not limited to, a right cylindrical profile (FIG. 7B) and a cylinder with a necked spherical tip (FIG. 7C). Such profiles can be implemented with full length fins, fins extending from a base portion, or with capped fins.

Figure 8:
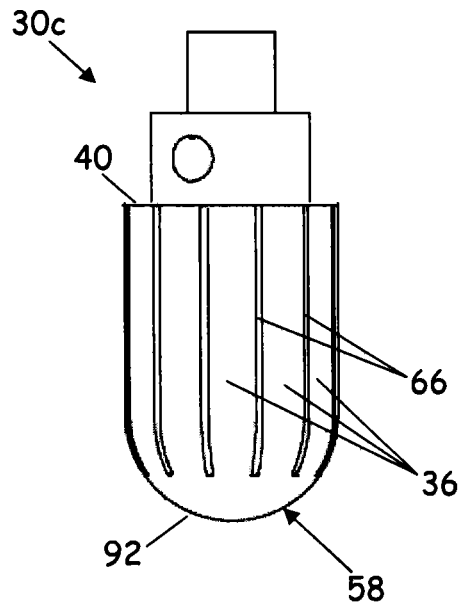
FIG. 8 is an elevation view of a capped irrigated finned ablation head in an embodiment of the invention.
Figure 8A:
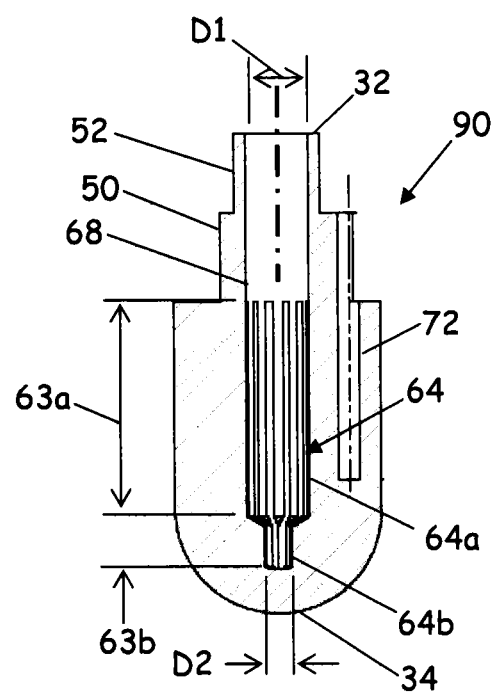
FIG. 8A is a sectional view of the capped irrigated finned ablation head of FIG. 8.
Figure 9:
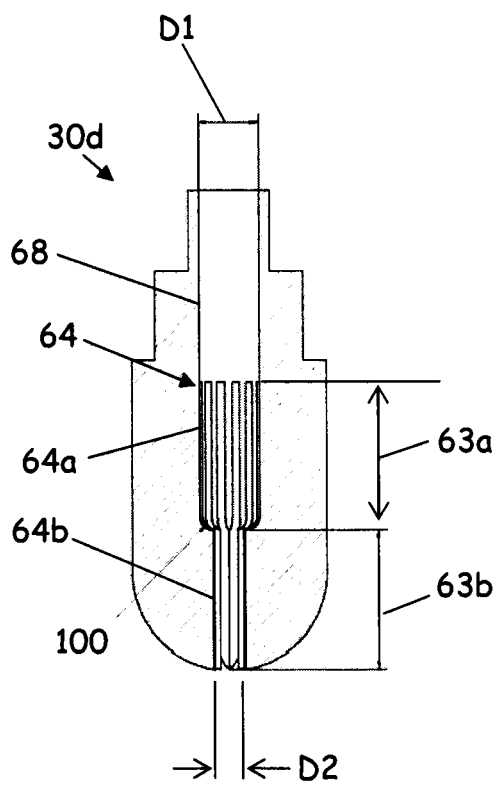
FIG. 9 is a sectional view of a irrigated finned ablation head with a central passageway having a radiused transition in an embodiment of the invention.
Figure 10:
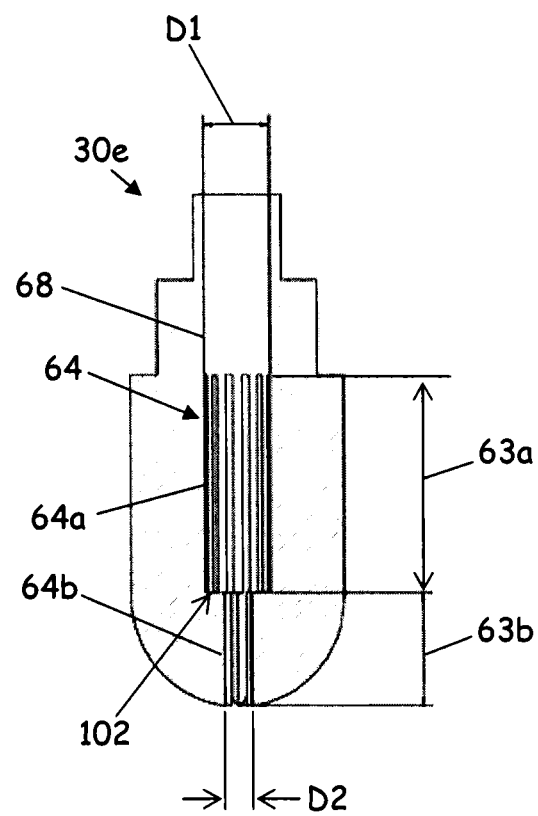
FIG. 10 is a sectional view of a irrigated finned ablation head with a central passageway having a step transition in an embodiment of the invention.
Figure 11:
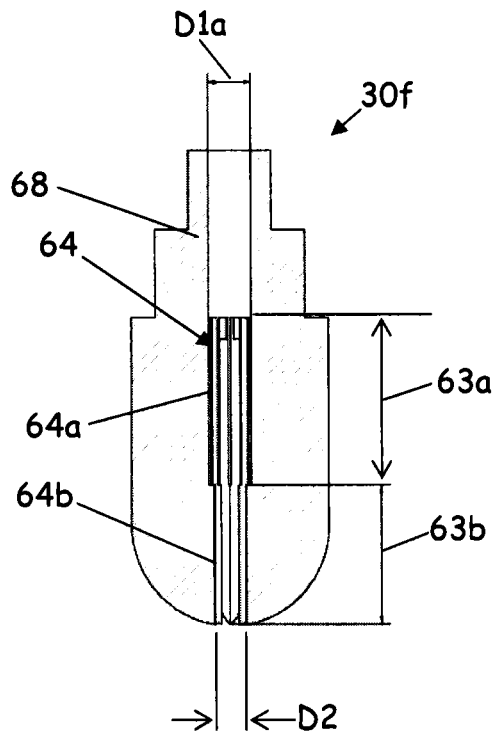
FIG. 11 is a sectional view of a irrigated finned ablation head with a central passageway having a reduced passage diameter in an embodiment of the invention.
Figure 12:
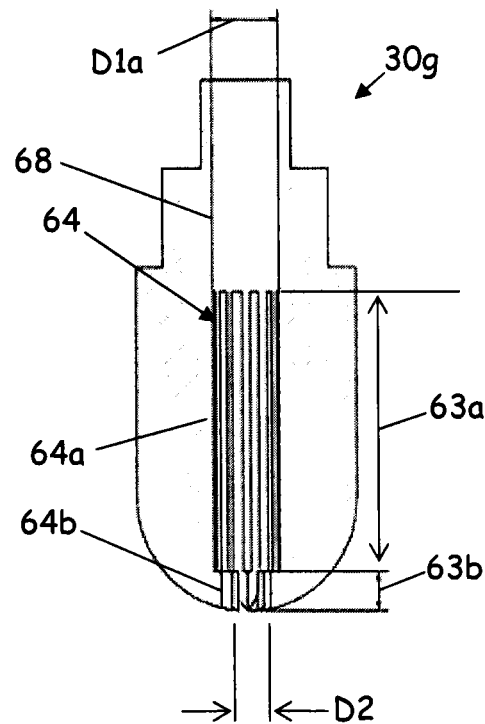
FIG. 12 is a sectional view of a irrigated finned ablation head with a central passageway having a longer proximal portion in an embodiment of the invention.
Figure 13:
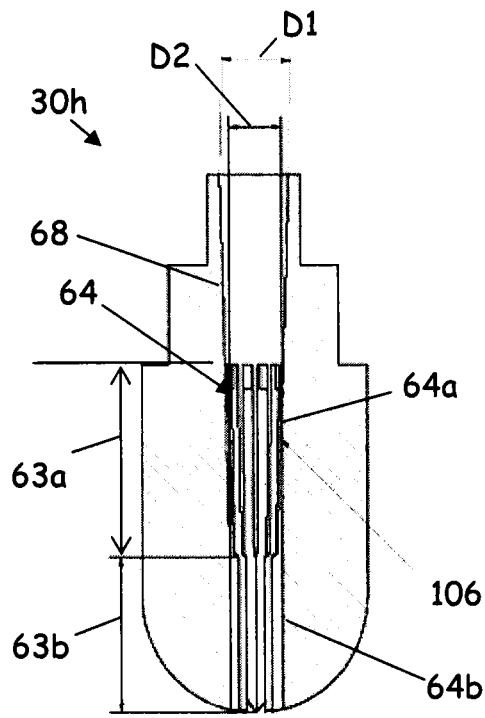
FIG. 13 is a sectional view of a irrigated finned ablation head with a central passageway having a tapered proximal portion in an embodiment of the invention.

Referring to FIGS. 8 and 8A, a capped finned ablation head 30c that is irrigated is depicted in an embodiment of the invention. The capped finned ablation head 30c includes many of the same aspects of the irrigated finned ablation heads 30a, identified with the same numerical reference numbers. The capped finned ablation head 30c also includes a cap portion 92 that connects all the radial fins 36 at the distal portion 35. The presence of the cap portion 92 seals off the central passageway 64 so that there is no opening on the central axis 38 at the distal extremity 34. The cap portion 92 can be integrally formed with (i.e., "unitary" with) the radial fins 36, or instead joined to the radial fins 36 by a soldering, brazing or other fusion process.

In operation, the capped finned ablation head 30c directs more coolant over the radial fins 36 at a given flow rate. Another characteristic of the radial fins 36 of finned ablation head 30c is that the fins extend through the base portion 40, an aspect that can be incorporated into any of the irrigated finned ablation heads 30.

Referring to FIGS. 9 through 14, alternative configurations for the central lumen 68 and central passageway 64 for irrigated finned ablation heads 30d-30i are depicted in embodiments of the invention. For example, different arrangements for the transition between the proximal and distal portions 64a and 64b of the central passageway 64 can be implemented. For irrigated finned ablation heads 30d and 30e, a spherical or radiused transition 100 (FIG. 9) or a step transition 102 (FIG. 10) are depicted defined, respectively, both of which are alternatives to the inclined transition 104 of the irrigated finned ablation head 30a depicted in FIG. 5A. In other embodiments, the diameter D1 of the proximal portion 64a can be altered, for example the diameter D1a depicted in the irrigated finned ablation head 30f of FIG. 11, which is of reduced dimension compared to diameter D1 of FIG. 5A. The relative lengths 63a and 63b of the proximal and distal portions 64a and 64b can also be tailored to provide a desired flow characteristic (e.g., the length 63b can be reduced and the length 63a increased, as depicted in the irrigated finned ablation head 30g of FIG. 12).

In other embodiments, the central passageway 64 is characterized as having a continuously variable diameter over at least a portion of the length. For the irrigated finned ablation head 30h of FIG. 13, for example, the proximal portion 64a of the central passageway 64 defines a tapered or conical profile 106 that extends to the central lumen 68, wherein the diameter linearly decreases from the diameter D1 at the inlet to the central lumen 68 to the diameter D2 at the inlet to the distal portion 64b.

Figure 14:
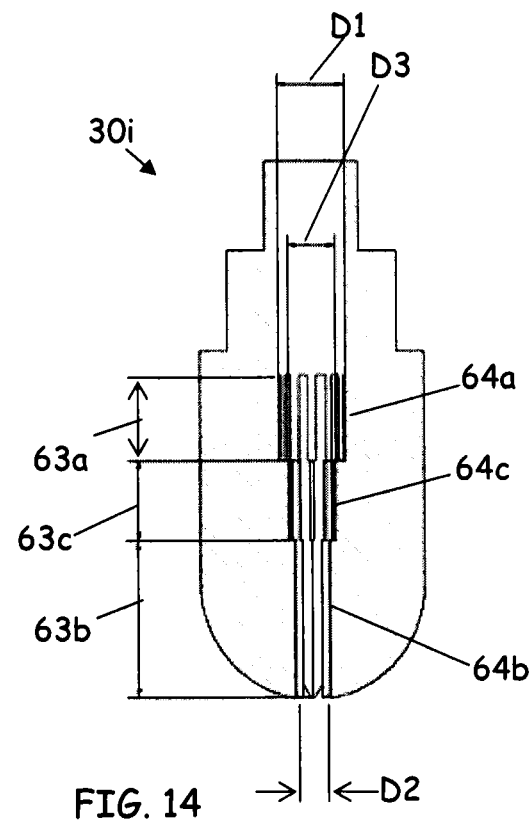
FIG. 14 is a sectional view of a irrigated finned ablation head with a central passageway having multiple stepped portions in an embodiment of the invention.

Still other configurations can utilize more than two radii for the central passageway 64. In one embodiment, the central passageway 64 is characterized as having an intermediate portion 62c between the proximal and distal portions 62a and 62b, the intermediate portion having a length 63c and a diameter D3 (FIG. 14).

Functionally, the radial flow distribution along the central axis 38, as well as the axial flow exiting the opening 65b at the distal extremity 34 of the irrigated finned ablation heads 30 can be affected by the configuration of the central lumen 68 and central passageway 64. For example, the different arrangements for the transition between the proximal and distal portions 64a and 64b of the central passageway 64 of the irrigated finned ablation heads 30 depicted in FIGS. 6, 9 and 10 can cause relatively more or less head loss as fluid flows through the transition. It is expected that the gradual transitions of FIGS. 6 and 9 generally causing less head loss than the step transition of FIG. 10. Changes in the head loss through the transitions affects the relative amount of the second portion 80b of the flow of irrigation fluid 80 that exits the opening 65b at the distal extremity 34 of the irrigated finned ablation heads 30.

The dimensions of the diameters D1, D2 and D3 of the central passageway 64 can also affect the flow distributions of the irrigated finned ablation head 30i. Larger diameters generally cause less head loss at a given flow rate than do smaller diameters. Also, for a given outer cylindrical diameter 61, an increase in the diameters D1, D2 and D3 reduces the radial dimension of the radial fins 36, which tends to reduce the flow resistance through the slots 66. Thus, increased dimensions for D1, D2 and D3 can reduce the head loss, and therefore lower the pump head requirements.

However, increased diameters D1, D2 and D3 and the attendant reduced head loss may not always be preferable. Consider that surface area-to-volume ratio A/V of the radial fins 36 may be reduced. Also, if a uniform flow profile is an objective of the design, the reduced flow resistance through the slots 66 may cause more of the first portion 80a of the flow of irrigation fluid 80 to exit near the proximal end 32 of the irrigated finned ablation head 30i than desired.

The lengths 63a, 63b and 63c of the respective portions 64a, 64b and 64c can also have an affect on head loss. For the embodiments depicted herein, where the diameter D1 of the proximal portion 64a is of larger diameter than either the diameter D2 of the distal portion 64b or the diameter D3 of the intermediate portion 64c, having the proximal portion 64a be of longer length than the intermediate and distal portions 64c and 64b will generally reduce head loss and can also result in greater flow of the second portion 80b of the flow of irrigation fluid 80.

In accordance with the principles above, general operating characteristics of the various depicted embodiments can be predicted relative to the embodiment depicted in FIG. 5A. The smaller diameter D1a depicted in FIG. 11 can be expected to produce a larger head loss for a given flow rate 80. The increased flow resistance of the central passageway 64 can tend to cause more of the flow of irrigation fluid 80 to flow away from the central passageway 64, thus increasing the first portion 80a of the flow of irrigation fluid 80. The larger diameters for both D1 and D2 in FIG. 12, in combination with the longer length of proximal portion 64a and the shorter length of the distal portion 64b, will likely cause a reduction in the head loss of the flow of irrigation fluid 80 and cause the second portion 80b to be increased relative to the configuration of FIG. 5A. The conical profile 106 of FIG. 13, as well as the multi-step profile of FIG. 14, tends to cause the flow resistance of the central passageway to increase from proximal to distal, resulting in more radial outward flow proximally than in the configuration of FIG. SA, and will also likely result in greater head loss for a given the flow of irrigation fluid 80.

Figure 15A:
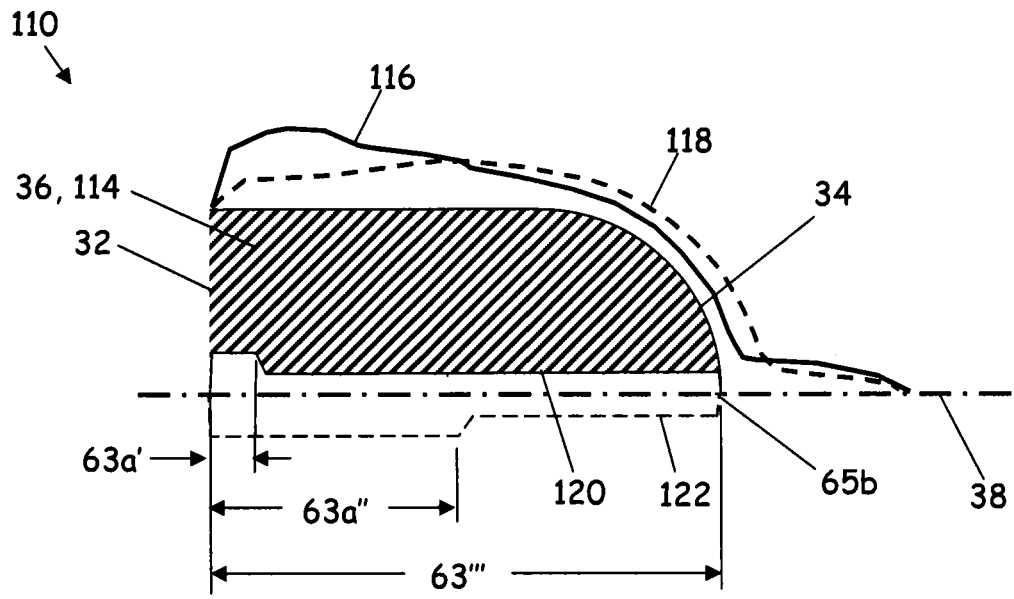
FIG. 15A is a graph illustrating the effect on the velocity profiles by varying the lengths of an increased-diameter proximal portion according to embodiments of the invention.
Figure 15B:
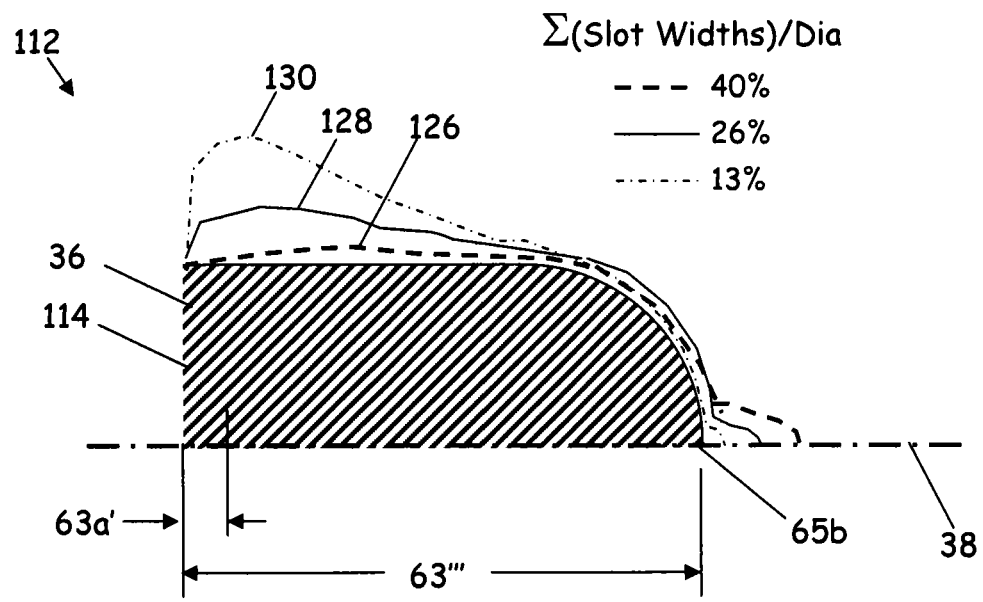
FIG. 15B is a graph illustrating the effect on the velocity profiles by varying the slot width according to embodiments of the invention.

Referring to FIGS. 15A and 15B, representative velocity profile characteristics 110 and 112, derived from computational fluid dynamic (CFD) simulations, are depicted for various embodiments of the invention. Each profile characteristic 110 and 112 includes an inset 114 of a partial sectional view of the radial fin 36 of a irrigated finned ablation head 30. The CFD simulations presented in FIGS. 15A and 15B modeled a 6-fin ablation head (FIG. 6) with full length radial fins (i.e., no cap portion) having a length of 3.3 mm extending from a 0.2 mm base.

The velocity profile characteristic 110 presents qualitative depictions of two velocity profiles 116 and 118. Velocity profile 116 is represented by a solid line and was generated for a proximal portion 64a having a length 63a' that is about 6% of the total length 63 of the central passageway 64 (i.e., 0.2 mm proximal length/3.5 mm total length). A profile 120 of this passageway is schematically represented on the inset 114. Velocity profile 118 is represented by the dashed line and was generated for a proximal portion 64 having a length 63a" that is about 50% of the total length 63''' (1.6 mm proximal length/3.5 mm total length). A profile 122 of this passageway is schematically represented in dashed line on the opposing side of the central axis 38 to profile 120. The dimensions recited above for 63a', 63a" and 63''' are representative and non-limiting. The flow rates modeled for the simulations represented in FIG. 15A was 30 cubic centimeters per minute (ccm).

Velocity profile 118 is generally more uniform than velocity profile 116. The velocity profile 116, produced by the shorter length 63a', is more pronounced (i.e., has higher velocities) near the proximal end than the velocity profile 118, produced by the longer length 63a". Both are characterized as having a high velocity relative to their respective profiles 116 and 118 at the opening 65b of the distal end 34.

The velocity profile characteristic 112 presents qualitative velocity profiles 126, 128 and 130, represented by dashed, solid and phantom lines, respectively. All three velocity profiles 126, 128 and 130 were generated for the proximal portion 64a having the length 63a' of about 6% of the total length 63''' (i.e., 0.2 mm proximal length/3.5 mm total length). The difference between the simulations that produced the velocity profiles 126, 128 and 130 is the modeled slot width 67 (FIG. 6A). Expressed in terms of a normalized cumulative width (i.e., the sum of the slot widths divided by the diameter of the ablation head), the velocity profiles 126 was generated assuming a slot width of 100 μm, whereas the velocity profile 126, 128 and 130 were generated assuming normalized cumulative slot widths of 13%, 26% and 40% respectively. The actual dimensions used in the CFD simulations were 50 μm, 100 μm and 150 μm, respectively, which, for the 6 slots modeled amounts to cumulative slot widths of 300 μm, 600 μm and 900 μm, respectively. The diameter of the cylindrical portion of the irrigated finned ablation head was 2.3 mm. The flow rate modeled for the results presented in FIG. 15B was 15 ccm.

In some embodiments, the central passageway 64 can be of a single diameter that extends the entire length 63. As discussed above, the diameter D2 can be a function of the slot widths 67 rather than being specifically formed to a given dimension, because the distal portion 64a of the central passageway 64 in some embodiments is the result of the confluence of the plurality of slots 66. Where the distal portion 64 is so formed, the viability of a single-diameter central passageway 64 depends partially on the slot widths 67 and also on the number of slots 66. Larger slot widths 67 will create a larger central passageway 64; a larger number of slots 66 for a given slot width 67 will create more lateral flow, thereby reducing the amount of fluid that reaches the opening 65b. It is noted that an objective of the irrigated finned ablation head is to keep the interface distal extremity 34 and the target tissue adequately cooled, because this region experiences the greatest current density as electric current passes from the irrigated finned ablation head to the target tissue. Therefore, it is desirable to have purging flow through all portions of all slots 66 adequate to provide convective cooling of the distal extremity 34. Another consideration, however, is to maintain an adequate pressure differential between the internal passages (central passageway and slots) and the ambient environment surrounding the target tissue. If there are zones where the slots 66 are not adequately pressurized, blood can gather in the slots 66 when in contact with the target tissue and form clots that later become entrained in the blood stream. Slot widths 67 of smaller dimension provide greater pressures at a given flow rate. However, for smaller slot widths 67, a proximal portion 64a of at least some length 63a might be required to attain adequate purging flows through the distal portion 35 of the irrigated finned ablation heads 30. (Such concern, of course, is reduced for the capped irrigated finned ablation heads, e.g. capped finned ablation head 30c.) We have found, by way of non-limiting example, that the irrigated finned ablation head 30b (i.e. having six radial fins) when modeled with slot widths 67 of 50 μm, should have a proximal portion 64a having a length 63a of at least 0.2 mm to assure adequate purging of the irrigated finned ablation head 30b.

For a given irrigation flow rate, the velocities and the pressure or head requirements increased with decreasing slot widths.

However, the general shape of the velocity profiles 126, 128 and 130 vary substantially with the slot width. Velocity profile 126 (greatest cumulative slot width) has a maximum velocity at a location along the central axis 38 that is at about ⅓ of the total length 63''' from the proximal end 32. The velocity profile 130 (smallest cumulative slot width), on the other hand, has a maximum velocity closer to about ⅒ of the total length 63''' from the proximal end. Velocity profile 128 (intermediate cumulative slot width) has a maximum velocity at a location between the velocity profiles 126 and 130. The peak velocities are also more pronounced (i.e., greater relative to the overall profile) as the cumulative slot width decreases.

Another trend can be observed at the opening 65b of the distal end 34. Wider slot widths also create a more pronounced profile at the exit opening 65b. A high velocity/flow at the exit opening 65b can be a disadvantage because of local cooling of the target tissue that the process is attempting to ablate. The narrower slit widths not only provide pronounced velocity profiles and the attendant enhancement of the convective coupling in the proximal portion 33 of the irrigated finned ablation head s 30, but also reduces the amount and velocity of the irrigation fluid that passes through the opening 65b, thereby reducing the attendant cooling of the target tissue that is under ablation.

While the invention is amenable to various modifications and alternative forms, specifics thereof have been shown by way of example in the drawings and described in detail. It is understood, however, that the intention is not to limit the invention to the particular embodiments described. On the contrary, the intention is to cover all modifications, equivalents, and alternatives falling within the spirit and scope of the invention as defined by the appended claims.

For purposes of interpreting the claims for the invention, it is expressly intended that the provisions of Section 112, sixth paragraph of 35 U.S.C. are not to be invoked unless the specific terms "means for" or "step for" are recited in the subject claims.

What is claimed is:

1. An ablation catheter tip, comprising:
    a core member that extends along a longitudinal axis, wherein the core member includes a base portion and a cap portion and a central passageway that extends along a portion of the longitudinal axis;
    a plurality of axially elongated radial fins that extend from the base portion to the cap portion; and
    a plurality of axially elongated slots defined by the plurality of axially elongated radial fins, wherein the plurality of axially elongated slots extend from the base portion to the cap portion, and wherein the plurality of axially elongated slots extend transversely with respect to the portion of the longitudinal axis from the central passageway to an exterior of the core member such that the slots are defined between each pair of the plurality of axially elongated radial fins and extend from the central passageway to the exterior of the core member, between each pair of the plurality of axially elongated radial fins, wherein the central passageway and the exterior of the core member are in fluid communication via the axially elongated slots.

2. The ablation catheter tip of claim 1, wherein a tangential width of each of the plurality of axially elongated slots is less than an axial length of each of the plurality of axially elongated slots.

3. The ablation catheter tip of claim 2, wherein each of the plurality of axially elongated slots:
    extends between the central passageway and an outer surface of the core member; and
    defines a plane that is inclusive of the longitudinal axis of the core member and extends along each of the plurality of axially elongated slots.

4. The ablation catheter tip of claim 1, wherein the cap portion is integrally formed with each of the plurality of axially elongated radial fins.

5. The ablation catheter tip of claim 1, wherein the central passageway is formed by a confluence of the plurality of axially elongated slots.

6. The ablation catheter tip of claim 1, wherein each of the plurality of axially elongated slots extend along an entirety of a length between the base portion and the cap portion.

7. An ablation catheter tip, comprising:
    a core member that extends along a longitudinal axis, wherein the core member includes a base portion and a cap portion and a central passageway that extends along a portion of the longitudinal axis;
    a plurality of axially elongated radial fins that extend from the base portion to the cap portion, wherein the plurality of axially elongated radial fins include interior faces that define the central passageway; and
    a plurality of axially elongated slots defined by the plurality of axially elongated radial fins, wherein the plurality of axially elongated slots extend along an entirety of a length from the base portion to the cap portion, and wherein the plurality of axially elongated slots extend from the central passageway to an outer surface of the core member and are defined between each pair of the plurality of axially elongated radial fins, wherein the central passageway and the exterior of the core member are in fluid communication via the axially elongated slots.

8. The ablation catheter tip of claim 7, wherein:
    the plurality of axially elongated radial fins extend continuously from the base portion to the cap portion; and
    the plurality of axially elongated slots extend continuously from the base portion to the cap portion.

9. The ablation catheter tip of claim 7, wherein the central passageway extends along a length of the plurality of axially elongated radial fins.

10. The ablation catheter tip of claim 7, wherein the plurality of axially elongated slots extend along a majority of a longitudinal length of the core member.

11. The ablation catheter tip of claim 10, wherein:
    each of the plurality of axially elongated slots is diametrically opposed from a corresponding axially elongated slot; and
    each of the plurality of axially elongated slots and the corresponding diametrically opposed axially elongated slot define a plane that is inclusive of the longitudinal axis of the core member.

* * * * *